United States Patent [19]

Krumhansl

[11] 4,300,909
[45] Nov. 17, 1981

[54] PROCESS CONTROL

[76] Inventor: Mark U. Krumhansl, 1811 Bent Twig, Tustin, Calif. 92680

[21] Appl. No.: 180,441

[22] Filed: Aug. 22, 1980

[51] Int. Cl.³ .................... G01N 1/14; G01N 11/02; G01N 33/18
[52] U.S. Cl. .................. 23/230 A; 422/62; 422/105; 422/110; 422/112; 364/500
[58] Field of Search ............ 23/230 A; 422/62, 67; 364/500, 803, 105; 422/105, 110, 112; 73/205 R

[56] References Cited

U.S. PATENT DOCUMENTS

| | | | |
|---|---|---|---|
| 3,721,253 | 3/1973 | Remke | 422/62 X |
| 4,053,743 | 10/1977 | Niemi | 23/230 A |
| 4,069,413 | 1/1978 | Rutledge et al. | 23/230 A |
| 4,094,959 | 6/1978 | Ball et al. | 23/230 A |

Primary Examiner—Ronald Serwin
Attorney, Agent, or Firm—Grover A. Frater

[57] ABSTRACT

A general purpose apparatus for measuring the chemical and physical state of flowing liquid materials and chemical additives and for introducing chemical materials to the stream uses a Venturi or other apparatus in which differential pressure is developed as an incident to fluid flow. It is arranged to be used both as a sample pump, a chemical additive pump, and as a differential pressure meter for use in calculating flow rates. The process method includes chemical addition at rates determined by pressure differential at the Venturi and for times which bear a selected relation to that differential pressure, temperature and the chemical state of the liquid. It also includes special temperature comparisons and flushing of chemical addition lines on an optional basis.

23 Claims, 3 Drawing Figures

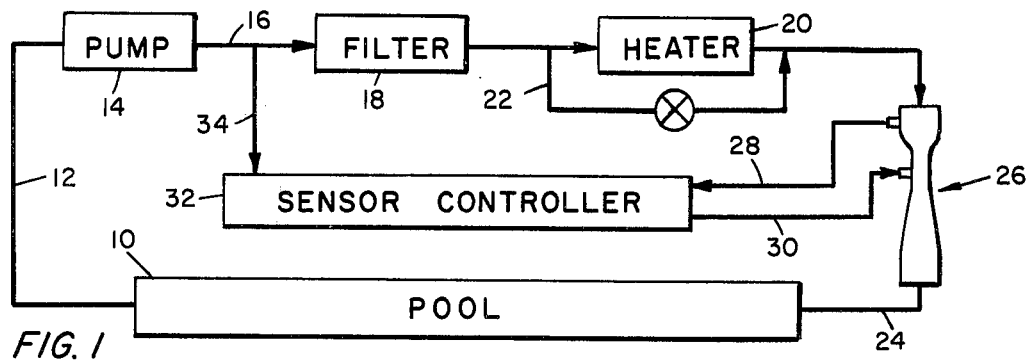

FIG. 1

| FUNCTION / VALVE NUMBER | V1 | V2 | V3 | V4 | V5 | V6 |
|---|---|---|---|---|---|---|
| MEASURE DIFFERENTIAL PRESSURE | 0 | 0 | 0 | 0 | 0 | 0 |
| MEASURE CHEMICAL STATE OF FLOW | X OR | 0 | 0 | 0 | 0 | |
| MONITOR CHEMICAL ADDITION | X OR | | 1 OF 3 | | | 0 |
| CALIBRATE PRESSURE TRANSDUCER | 0 | 1 | 0 | 0 | 0 | 1 |
| MEASURE TEMPERATURE (UP STREAM) | 1 | 0 | 0 | 0 | 0 | 1 |
| MEASURE TEMPERATURE (DOWN STREAM) | 0 | 1 | 0 | 0 | 0 | 1 |
| ADD BASE OR ACID | X OR | 1 | 0 | 0 | 0 | |
| ADD CHLORINE 1 | X OR | 0 | 1 | 0 | 0 | |
| ADD CHLORINE 2 | X OR | 0 | 0 | 1 | 0 | |
| RINSE, HIGH PRESSURE | 1 | 0 | 0 | 0 | 0 | 1 |
| RINSE, LOW PRESSURE | 0 | 1 | 0 | 0 | 0 | 1 |
| LEGEND: 0 = CLOSED  1 = OPENED    X OR = ONE OR THE OTHER | | | | | | |

FIG. 3

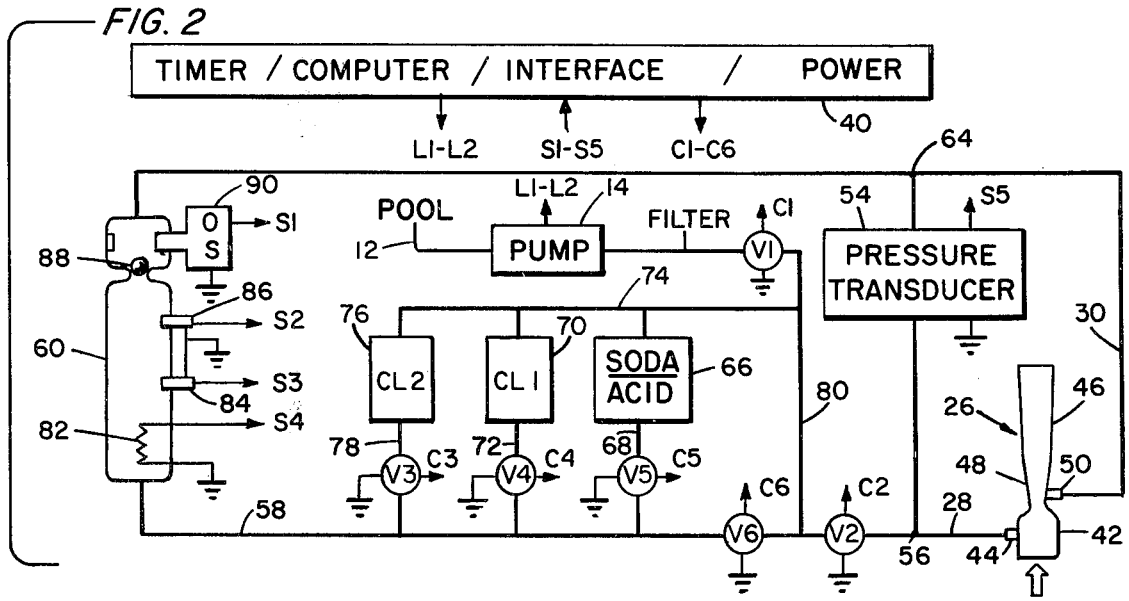

FIG. 2

PROCESS CONTROL

TECHNICAL FIELD

This invention relates to methods and apparatus for measuring the chemical state of a fluid and the physical state of both the fluid and an apparatus for treating it, furnishing that information to an algorithm solving apparatus, and accomplishing process action in response to signals from the algorithm solving apparatus.

BACKGROUND OF THE INVENTION

There are many processes that involve the addition of chemical substances to fluids in which the amount of added material is to be adjusted according to physical and chemical criteria. Some of those processes will require a degree of treatment, either physical or chemical, which is determined by the state of the treatment apparatus. Examples can be found in hydroponic gardening, drug manufacture, maintenance of decorative pools, marine animal "farming," and others.

Another, and a very important example, is found in the processing of the water in swimming pools. In addition to its recreational use, the water in swimming pools represents a very important energy storage medium in private and public energy conservation systems. Because of the large volume of water in a swimming pool, it is capable of absorbing, storing and releasing very large quantities of heat with relatively small temperature changes. That makes it specially useful as a place in which to store heat when cooling living spaces and as a source of heat when heating living spaces. And, the pool is an excellent place in which to store solar energy with or without an energy collection cover, as a solar energy collector.

On the other hand, to use a swimming pool as a heat storage element results in pool water temperatures that are higher at times than the temperatures that are maintained for recreational use alone. Algae, pathenogenic bacteria, and pool water chemistry control are likely to be a more difficult problem in the swimming pool that also serves as a thermal energy storage unit.

The problem of dirt and debris removal remains unchanged except that the usage of pool covers, which also enhance solar energy collection, results in the pool being covered for more of the time. This is offset by the fact that the pool water is subsequently warmer and recreational use is feasible for more months of each year. Economic and social factors dictate that most heat storage water pools will have an exposed solar surface and will utilize removable covers for additional recreational as well as heat storage use.

Both mechanical filtration and chemical management are required, and at the least, the chemical processing will need to be much more precisely controlled. Mechanical filtration must be controlled if the amount of energy expended on water circulation is to be minimized. The best criterion for filtration is the "turnover" frequency when all of the pool water is moved through the filter based upon the conditions of local environment. The "turnover" frequency having been selected, and the pool volume being known, the parameters are volumetric pumping rate and time. Because the size of pumps and filters is fixed at each installation, the practical variable is time.

On the chemical side, the major variables are pH and the need for a bacteriacide and algicide. In practice, some form of sanitizer, typically chlorine is used to control bacteria and algae. The effectiveness of the chlorine, the swimming quality of the water, and the corrosion rate is determined by controlling pH. In each geographic area, pH tends to change in one direction or the other requiring only addition of acid or base as required. In most cases it is acid that needs to be added. It is much preferred that these materials be added at a very slow rate over a long period except when chlorine "shocking" is required. With time, algae and bacteria mutants, resistant to the chlorine treatment, will survive and multiply in the pool. To kill the individuals of that strain, a massive dose of a different bacteriacide and algicide is applied to the pool. In most cases the "shocking" dose is formed by a chlorine component other than what is used for sanitizing maintenance control.

The measurement and control of pool water composition has been beyond the capability of most pool owners unless the process is reduced to simplified approximations. In most cases, control is accomplished as a function of time. Measurements and chemical additions are made daily, at best, and more often on the one or two days of the week that the pool maintenance person makes his rounds. Chemical additions are made in batches. The concentrations that result cause excessive corrosion, both in the pool and in the water circulation system. Breakdown of heating and filtration systems may go undetected for long periods. Because they operate only periodically, the fact that these units are not operating when the pool is being serviced may be interpreted as being normal.

This swimming pool example is only one of many in which combined physical and chemical control is exercised. It is, however, a very important example, not only because of the very large number of existing private swimming and spa pools, but because those pools represent an important existing facility that is easily applied to the problem of conserving energy and utilizing solar energy.

The availability of microprocessors has made it possible to solve very complex algorithms at far less cost than was possible with discrete digital and analog devices and the relays of prior times. The microprocessor has not always simplified the task of sensing conditions and taking corrective actions. Sometimes it leads to greater complications. This invention is related to those tasks, the tasks of sensing conditions and applying the controlling actions to be accomplished, in most cases, in conjunction with algorithm solution, whether by the new computers or the old discrete components.

SUMMARY OF THE INVENTION

It is an object of this invention to provide an improved method and apparatus for sensing in connection with the processing of fluid materials.

A related object is to provide an improved method and apparatus for accomplishing controlling action in connection with the processing of fluid materials.

Another object is to provide improved methods and means for accomplishing chemical control and filtering of swimming pool water generally, and in the circumstance in which the pool water is used as a thermal energy storage facility.

Another object is to utilize the energy of a flow of the liquid being processed to measure flow rate in terms of flow produced differential pressure and to use that differential pressure to add chemicals at a rate which varies with flow rate of the liquid being processed. In this connection, it is preferred to employ a Venturi both as a flowmeter and as an educing pump by which chemicals are added to the stream of liquid. To utilize such a device is another object and feature of the invention.

In pool water processing, and in some other processes, materials are added which are better not mixed unless extremely diluted. It is a feature of the invention to utilize the differential pressure developed in a differential pressure producer to flush chemicals from the chemical adding circuit prior to the addition of others, if any, so that only a single chemical adding circuit is required. Alternatively, the force of processed liquid flow can be employed to flush the chemical adding circuit.

One of the advantages of the microprocessor is that it can solve many algorithms provided, of course, that an adequate data sensing apparatus and method of implementing solutions are available. Another object of the invention is to provide a system which is particularly efficient in that a minimum of apparatus is employed to provide a large amount of data. A related object is to provide a data collection system which is capable of taking advantage of the ability in modern algorithm solvers of storing information so that decision making and corrective actions need not be accomplished simultaneously with data collection.

More particularly, it is an object to provide a means for comparing temperatures upstream and downstream from the heating or cooling apparatus, to provide a means for comparing chemical levels thus to sense and monitor chemical additions even when additions are made at very low rates for long periods, to provide a practical means for introducing chemicals that must be or are best stored in solid form, to provide for automatic downstream chemical addition without the need for positive displacement pumpt, to provide electrode temperature compensation, compare upstream and downstream chemical levels and temperatures, and to provide super chlorination or "shocking" on the basis of thermal history rather than the mere passage of time.

These and other objects and advantages of the invention, which will hereinafter become apparent, including a pressure transducer calibrating capability, are accomplished, at least in part, by the provision of an apparatus which includes a "flowpath" to be connected in a stream of the fluid to be processed. The differential pressure producer, usually a Venturi, is provided with a high pressure port upstream of the Venturi throat and a low pressure port at the throat. The flowpath between those ports can be opened for chemical and fluid temperature sensing, using differential pressure between the ports to induce a shunted flow through the flowpath and its monitoring sensors. The same flowpath is arranged to draw chemicals into the system to be monitored and to be discharged into the throat of Venturi and mixed thoroughly in the main stream of liquid flow and to flush the chemicals from within the flowpath.

The "flowpath" includes temperature, chemical and optical condition sensors in addition to chemical input means upstream from the sensors. Thus arranged, the flowpath is connected with its outlet end downstream from the pumping, filtering and heating apparatus. In the invention, the input end of the flowpath is selectively connected upstream from filtering and heating apparatus or downstream from that apparatus. That arrangement permits "before and after" comparisons of temperature and chemical condition that are separated by either long or short time periods. To provide such an arrangement is among the objects of the invention. It permits servo or feedback control with anticipation, despite the fact that the reaction cycle is long, and, using the same apparatus, its permits monitoring of the corrective action.

In the preferred form for use in processing swimming pool water, a pump propels water through the Venturi, differential pressure producer, and such auxiliary apparatus as a heater and filter and solar units. Valves are provided by which the measurement and chemical addition flowpath may be connected between the pump outlet or inlet and either of the Venturi ports, or may be connected across said ports.

The method includes addition of chemicals in quantities and for times that bear a selected relation to differential Venturi port pressures and the chemical state of the liquid material temperatures and, in some cases, time alone.

It is to be understood that the invention has application beyond swimming pool treatment and control. For example, it is applicable to the treatment of irrigation water with fertilizers, fungicides and pesticides, and to the processing of drinking water and to the processing of liquids other than water.

THE DRAWINGS

In the drawings:

FIG. 1 is a block diagram of the preferred form of the invention applied to the sensing and treatment of the water of a swimming pool;

FIG. 2 is a more detailed diagram of a portion of the apparatus of FIG. 1 which is partly in schematic and partly in block diagram form; and FIG. 3 is a chart of the condition of the valves of FIG. 2 in various operating circumstances.

DETAILED DESCRIPTION OF THE DRAWINGS

While the invention has many other uses, a major application lies in the processing of pool water. The embodiment of the invention selected for illustration is described in relation to that use, and is the best mode for the invention that is now known.

FIG. 1 is a diagram of a conventional pool water processing system modified to incorporate the invention. The pool is generally designated 10. Water from the pool is withdrawn by an outlet line 12 and a pump 14 the discharge of which is conducted by a line 16 to a filtration unit 18. After leaving the filtration unit, pool water flows through a heater unit 20, or bypasses the heater by flowing through a bypass circuit 22, depending upon whether the pool water is to be heated. Upon leaving the heater or the bypass circuit, pool water is returned to the pool by a line 24. In the invention a means is provided for measuring the flow rate of fluid through that circuit, or for measuring some parameter which is a measure of flow rate. In addition, a means is included by which the energy that is stored in the flow of liquid to be processed is utilized to draw processing materials into the flow stream.

It is a feature of the invention to provide a measure of flow rate by developing a differential pressure in a Venturi mechanism or its equivalent in the sense that a differential pressure is produced by the flow.

In FIG. 1, the element 26 is a Venturi-type flow meter or its equivalent which has a high pressure port connected to a line 28 and a low pressure inlet port connected to a line 30. Those are fluid flow lines that carry quantities of the liquid to be processed, here the pool water, to and from an apparatus 32 which is designated a "SENSOR CONTROLLER" and which is shown in greater detail in FIG. 2. The sensor controller unit has connection to the outlet line 16 of the pump 14 by a flow conduit 34. In certain circumstances flow through that line 34 flows through the sensor controller unit 32 and return line 30.

One function of the sensor controller unit 32 is to measure the pressure differential between the outlet and the inlet ports of the flow meter 26. Another function of the sensor controller in the preferred embodiment is to receive liquid from the flow meter line 28 and to return that liquid via line 30 after having sensed the chemical and physical conditions of the pool water. In preferred form, the pH level of the water is measured, along with the level of algicide and bacteriacide material in the water. Within the controller a means is provided for adding processing chemicals to the flow of liquid as it proceeds from line 28 to the return line 30. A higher pressure differential is developed across the pump 14, and in the preferred embodiment, the flow line 34 is available to provide a supply of the pool water to the sensor controller unit for chemical and physical analysis. In the preferred form that physical analysis includes a measurement of temperature and a means for compensating for a drift in the chemical sensors.

The filter and the heater and the pool have been omitted from FIG. 2. The pump 14 is shown along with the Venturi flow meter 26. Except for the computer unit 40, the remainder of what is shown in FIG. 2 forms the sensor controller unit 32 of FIG. 1. The Venturi flow meter includes an inlet end 42 which is formed with a high pressure or outlet sensing port 44. Between the inlet end 42 and the outlet end 46 of the flow meter there is an intermediate portion 48 which has reduced flow area. This is the Venturi restriction, and a throat or inlet sensing port 50 communicates with the interior of that reduced area region. A sensing flow line 28 extends from the pressure port 44 to one side of a pressure transducer 54. The throat port 50 is connected to the other side of the pressure transducer 54 by the return line 30.

No fluid flows through the transducer. Instead, the transducer simply measures the pressure differential between the outlet and inlet ports of the flow meter, and provides an output signal, S5, whose value is indicative of the magnitude of the pressure differential.

Except during calibration, pressure measurement is taken only when there is no contiguous fluid flow from high pressure outlet port or to throat inlet port of the flow meter. It is taken at a time when all valves are closed. Valves are included in a sensing and chemical addition flow path which extends from junction 56 in line 28 through valve V2, valve V6 and line 58 to a sensing assembly 60, and then by a line 62 to a junction 64 in the inlet line 30 to throat port 50. Thus, the sensing and chemical addition flow path includes line 28, valve V2, valve V6, line 58, sensing unit 60, line 62, and line 30. In this embodiment, there are three chemical sources. Source one is a container of soda or acid, and is designated 66. Soda or acid will be drawn into the sensing and chemical addition flow path through a chemical flow path 68 when the valve V5 is opened. The second source is numbered 70 and is connected by a chemical addition line 72 through the valve V4 to the sensing and chemical addition flow path. In this application the source 70 is the container for a form of chlorine C12 that is dissolved in water before being dispensed into the system, and the source for that water is the output of the Venturi 26 or pump 14. Water is delivered from the pump 14 to the source container 70 by valve V1 and a line 74. The chemical source 76 is a container which, in this embodiment, includes an alternative form of liquid algicide or bacterial material, here designated C12, which is used to "shock" the pool to kill any resistant strains of algae and bacteria that may have developed by mutation following the previous "shock" treatment. That chemical is then delivered to the sensing and corrective action flow path by a chemical addition line 78 through the normally closed valve V3. The valves V3, V4 and V5 respond to control signals that are applied to control lines C3, C4 and C5, respectively. The valve V2 responds to a signal on a control line C2, and valves V1 and V6 respond to signals on control line C1 and C6, respectively. The valve V1 is connected in a line 80 which extends from the output of pump 14 to line 74 and to a point in the sensing and chemical addition flow path which is downstream from the valve V2 but is upstream from valve V6 and the point at which chemicals are introduced into that flow path through valves V3, V4 or V5.

Valve V1 is open for flushing only when valves V2, V3, V4 or V5 is closed. When opened, it permits the flow of pool water from the outlet of pump 14 through valve V6 and that portion of the sensing and chemical addition flow line in which the sensing and chemical addition is accomplished. Flow through the line flushes it free of chemical additives and permits measurement of chemical levels and temperature of port water upstream from the filter and heater.

Flushing can be accomplished using water from port 44. Valves V1, V3, V4 and V5 are closed. Valves V2 and V6 are opened. This same valve condition permits measurement at unit 60 of temperature and chemical condition of the circulating water at the Venturi. In addition, this valve condition permits making calibration measurements to be used in calibrating the output of the differential pressure transducer as described below.

The sensing unit 60 is shown schematically. It consists of a flow path in which a number of sensors are mounted. The first of those sensors is numbered 82 and it comprises a thermistor network whose function is to alter the signal current, designated S4, whereby the temperature of the liquid contained in the sensing unit 60 is described. The sensor 84 is a conventional pH sensitive electrode. The magnitude of its output signal S3 indicates the pH value of the fluid in the unit 60. The sensor 86 is an ion selective electrode which measures the concentration of chlorine or bromine ions in the fluid contained within the unit 60. A signal indicative of that concentration is developed, and is here designated S2. In a separate section of the unit 60, which is separated from the initial flow path of the unit by a ball check valve 88, is an optical sensor labelled "OS," and designated 90. It is capable of adding chemicals to the fluid in the sensing unit and then measuring any resulting change in the color and transparency of the fluid. That section of the sensing unit is used in this application for measuring the concentration of nitrates and other materials. Other sensors may be included in the standard sensing unit which is thus arranged for application to a number of fluid processing tasks other than pool water treatment.

The control signals, C1 through C6 are developed in an interface section of computer unit 40 which also receives signals S1 through S5 and is arranged to apply power to the pump 14 by power lines L1 and L2. The computer unit also includes a timer which can be used by the computer to cause the interface section control to provide control signals 1 through 5 at selected times. The interface unit will have a form that depends upon the form of the computation section of computer 40. That section could comprise a relay control circuit of the kind that was popular before the advent of solid state digital devices. It could comprise discrete digital logic devices, but would more likely consist of a microprocessor capable of solving one or more algorithms the particular form of which forms no part of this invention and is not important here, except that it is a device which is capable of supplying control signals which vary as a function of time, temperature, differential pressure or chemical state, or combinations of those parameters. The output of a microprocessor is a digital signal the power in which is ordinarily insufficient to operate the several relays. One function of the interface unit is to amplify signal outputs from the computer to a level sufficient to actuate the valves. That is true, too, in the case of lines L1 and L2 which supply power to the pump 14. The microprocessor output will be insufficient to drive the pump. Instead, the computer will drive a power amplifier and relay which will open and close the power lines to the pump.

Each of the signals, S1 through S5, is in analog form. That is, the transparency and color sensor 90 and the ion selective sensor 86, and the pH sensor 84 and the thermistor 82, all provide analog outputs. The interface unit includes analog to digital converters which supply digital signals to the computer. The power amplifiers and the analog to digital converters that together form the interface unit need be no more than a collection of the control elements that are well known and readily available in the market place.

The major functions that are performed by the apparatus of FIGS. 1 and 2 are listed at the left in the chart of FIG. 3. The chart shows the condition of the several valves of this system during the performance of the different functions that can be performed. In the chart, a "0" means that the valve is closed, a "1" means that the valve is open. When it is desired to measure flow rate, or more properly, pressure differential across the Venturi ports, all valves are closed. When it is desired to make measurements with the sensing unit 60, the valves V3, V4 and V5 are opened or closed as indicated in FIG. 3, valve V6 is opened, and one or the other, but not both, of valves V1 and V2 are open. If temperature upstream is to be measured, valves V1 and V6 are opened and all others are closed. If downstream temperature is to be measured, valves V2 and V6 are opened and all others are closed. When adding soda, or acid, valves V5 and one of V1 or V2 is open, and the others are closed. When the algicide or bacteriacide, usually chlorine, is to be added, one of valves V1 or V2 is opened, valve V4 is opened, and the others are closed. When the pool is to be "shocked" or super chlorinated, valves V1 or V2 and V3 are opened and the remainder closed. After adding chemicals, it is a feature of the invention to rinse the sensing and corrective action flow path by opening valves V1 and V6 and closing the others. That will result in rinsing with high pressure water. If rinsing is to be accomplished with low pressure water, then valves V2 and V6 are opened and all the others are closed.

The differential pressure that is developed across ports 44 and 50 of the Venturi device 26 varies with flow rate through the Venturi. Consequently, the suction pressure available at port 50 draw chemicals into the main flow stream will be diminished as a function of flow rate reduction. The sensors in measuring unit 60 will indicate actual chemical input rate, and it is a simple matter to adjust the duration of chemical inlet valve opening to ensure proper chemical input. On the other hand, the availability of pressurizing liquid in the flushing line from port 50 and the pump 14 outlet has been used to advantage as a source of pressure in dissolving and forcing chemicals into the sensing and chemical addition flow path. To utilize the pressure developed at the outlet of the pump 14, valve V1 is opened and valves V2 and V6 are closed. To utilize port 50 pressure, valves V1 and V6 are closed and valve V2 is opened. The chart in FIG. 3 does not describe the circumstance in which the differential pressure developing device is used as a eductor because that mode of operation, in which all but one of valves V3, V4 and V5 are closed, is less applicable to pool water processing that the operational modes described in the chart.

Although I have shown and described certain specific embodiments of my invention, I am fully aware that many modifications thereof are possible. My invention, therefore, is not to be restricted except insofar as is necessitated by the prior art.

I claim:

1. For use with a system which includes a means for causing a flow of fluid material along a main flowpath, a chemical sensing and controlling unit, comprising:
pressure differential sensing means connected in said main flowpath and having a high pressure outlet port at its input side and a lower pressure inlet port downstream from said outlet port for developing a differential pressure between said ports the magnitude of which varies with flow rate along said main flowpath:
a sensing and chemical addition flowpath extending from said outlet port to said inlet port;
sensing means for measuring the chemical state of the fluid flowing in said sensing and chemical addition flowpath; and
chemical adding means for utilizing the flow of fluid in said sensing and chemical addition flowpath for introducing into said main flowpath quantities of a substance capable of altering said chemical state.

2. The invention defined in claim 1 which further comprises:
pressure measuring means for measuring the pressure differential between said ports: and
a flow control valve in said sensing and chemical addition flowpath for closing said flowpath at times when said pressure measuring means is utilized for measuring pressure differential.

3. The invention defined in claim 1 in which said chemical adding means includes a chemical source, a chemical flowpath along which said substance can flow to said sensing and chemical addition flowpath to a point upstream of said sensing means, and a chemical addition control valve in said chemical flowpath for selectively permitting and preventing flow through said chemical flowpath.

4. The invention defined in claim 3 which comprises:
a flow control valve in said sensing and chemical addition flowpath;

means for causing said flow control valve to be open for a period and said chemical addition valve to be open for a portion of said period and then to be closed for the remainder of said period whereby flow in said sensing and chemical addition flowpath is utilized in the addition of chemicals and then in the flushing of said sensing and chemical addition flowpath.

5. The invention defined in claim 3 which further comprises means for measuring the temperature of said liquid material and means for furnishing information about the temperature and chemical state of said liquid material to an algorithm solving apparatus and for actuating said chemical addition valve in response to signals from said algorithm solving apparatus.

6. The invention defined in claim 5 which further comprises:
   means in the form of a flow control valve in said sensing and chemical addition flowpath for closing said sensing and chemical addition flowpath; and
   pressure sensing means for measuring the pressure differential between said ports.

7. The invention defined in claim 1 which further comprises information furnishing means for furnishing information about the pressure differential between said ports to said algorithm solver and the chemical state of said liquid material to an algorithm solver and for actuating said chemical addition valve in response to signals from said algorithm solver.

8. The invention defined in claim 7 which further comprises means for measuring the temperature of said liquid material;
   said information furnishing means being effective to furnish information about the temperature of said liquid material to said algorithm solving means.

9. The invention defined in claim 1 in which said differential pressure measuring means comprises a Venturi and in which said means for causing flow comprises a pump and which further comprises means in the form of a flow line and valve for selectively connecting the upstream end of said sensing and chemical addition flowpath to the upstream side of said Venturi or the outlet of the pump.

10. The invention defined in claim 9 which comprises means for connecting said sensing and chemical addition flowpath across said ports when chemicals are being added thereto and for selectively reconnecting the inlet of said sensing and chemical addition flowpath to the output of said pump whereby to flush chemicals from said sensing and correction flowpath.

11. The invention defined in claim 9 which further comprises:
   means in said sensing and chemical addition flowpath for measuring the temperature of liquid flowing therethrough; and
   means for connecting said sensing and chemical addition flowpath in parallel with said ports while measuring the temperature of fluid flowing downstream of the pump and for connecting said flowpath between the outlet of the pump and the inlet port of the Venturi while measuring the temperature of the fluid emerging from the pump.

12. The invention defined in claim 1 in which said sensing means comprises means for measuring pH and temperature and the relative proportion of biocidal chemical in said fluid substance.

13. The invention defined in claim 12 in which said chemical adding means includes means for adding a chlorine bearing material and a pH adjusting material to said sensing and chemical addition flowpath at selected different times.

14. The method of processing fluid materials which comprises the steps of:
   forcing said fluid material to flow through a differential pressure producing device which is fitted with and outlet port and a downstream inlet port;
   interconnecting said ports through a flowpath such that a portion of said fluid material flows therethrough;
   measuring the chemical state of the fluid flowing through said flowpath; and
   subsequently introducing chemicals into said flowpath for a period bearing a selected relation to the measured chemical state of said fluid.

15. The method defined in claim 14 which comprises the further step of interrupting flow through said flowpath and measuring the pressure differential across said ports in the interval in which said flow is interrupted.

16. The invention defined in claim 15 in which the length of the period during which chemicals are added to the fluid has a selected relation to the pressure across said ports and the chemical state of said fluid at the beginning of said period.

17. The invention defined on claim 15 which includes the step of continuing flow through said flowpath after cessation of the addition of chemicals whereby to flush chemicals from said flowpath.

18. The invention defined in claim 17 in which the chemical added is an algicide in one chemical form and which comprises the added step of adding quantities of algicide in another chemical form in selected quantities and at selected intervals which are independent of said chemical state and pressure differential.

19. The invention defined in claim 16 in which the measurement of chemical state includes measurement of pH and the prevalence of sanitizing ions and in which the step of adding chemicals includes the addition of chlorine bearing material and one of acid or base.

20. The method defined in claim 16 in which the chemical state of fluid flowing in said flowpath is measured during the addition of chemicals to said flowpath and in which the length of the period over which chemicals are added to fluid flow through said flowpath has a selected relation to the chemical state so measured.

21. The invention defined in claim 9 in which said chemical adding means comprises means for utilizing suction developed at the low pressure side of said differential pressure sensing means for educting chemicals through said sensing and chemical addition flowpath into said main flowpath.

22. The invention defined in claim 9 in which said chemical adding means comprises means for utilizing pressure developed at one of the output of the pump and said outlet port for aiding in the introduction of chemicals into said main flowpath.

23. The method of calibrating a differential pressure measuring transducer which is connected across an apparatus in which a differential pressure, variable as a function of flow rate, is produced as an incident to flow and which method comprises the steps of:
   measuring pressure differential across said transducer in the absence of any significant flow in parallel with said apparatus;
   measuring pressure differential across said transducer in the presence of flow, substantially without resistance, in parallel with said apparatus; and
   adjusting the measurement taken in the absence of parallel flow by an amount which is a function of the measurement taken during the period of parallel flow.

* * * * *